(12) United States Patent
Sigmon, Jr. et al.

(10) Patent No.: US 12,733,789 B2
(45) Date of Patent: Sep. 15, 2026

(54) ENDOSCOPE HANDLE WITH CATHETER LOOP

(71) Applicant: Cook Medical Technologies LLC, Bloomington, IN (US)

(72) Inventors: John C. Sigmon, Jr., Winston-Salem, NC (US); Christopher A. Carruthers, Winston-Salem, NC (US); Marc Spencer, Winston-Salem, NC (US); Shaun D. Gittard, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 327 days.

(21) Appl. No.: 18/545,726

(22) Filed: Dec. 19, 2023

(65) Prior Publication Data

US 2024/0206706 A1 Jun. 27, 2024

Related U.S. Application Data

(60) Provisional application No. 63/476,747, filed on Dec. 22, 2022.

(51) Int. Cl.
*A61B 1/00* (2006.01)
*A61B 1/06* (2006.01)

(52) U.S. Cl.
CPC ...... *A61B 1/00066* (2013.01); *A61B 1/00087* (2013.01); *A61B 1/00098* (2013.01); *A61B 1/0676* (2013.01)

(58) Field of Classification Search
CPC ............ A61B 1/00013; A61B 1/00066; A61B 1/00163; A61B 1/0052; A61B 1/00119; A61B 1/00133
See application file for complete search history.

(56) References Cited

U.S. PATENT DOCUMENTS

| | | | | |
|---|---|---|---|---|
| 7,220,227 | B2 | 5/2007 | Sasaki et al. | |
| 8,998,825 | B2 | 4/2015 | Matsuno et al. | |
| 9,723,973 | B2 | 8/2017 | Dillon et al. | |
| 10,520,694 | B2 | 12/2019 | Chu et al. | |
| 10,823,923 | B2 | 11/2020 | Chu | |
| 10,918,402 | B2 * | 2/2021 | Chu | A61B 17/221 |
| 2006/0135846 | A1 | 6/2006 | Hunt | |

(Continued)

FOREIGN PATENT DOCUMENTS

WO WO 2010/067762 A1 6/2010

OTHER PUBLICATIONS

Partial European Search Report for corresponding European application No. 23219537.0 dated May 6, 2024, 12 pages.

(Continued)

*Primary Examiner* — Michael J Carey
*Assistant Examiner* — Dayton Hyun Jin Barker
(74) *Attorney, Agent, or Firm* — Vivacqua Crane, PLLC

(57) ABSTRACT

A scope system including a handle that may be changed from a locked configuration to an unlocked configuration by removing a removable handle lock is provided. The handle includes features for storage of a movable elongate member on the side of the handle when the handle is in the locked configuration. In the unlocked configuration, the movable elongate member can be connected to the handle to perform desired procedures.

20 Claims, 7 Drawing Sheets

(56) References Cited

U.S. PATENT DOCUMENTS

| | | | | |
|---|---|---|---|---|
| 2008/0262301 | A1* | 10/2008 | Gibbons | A61M 25/0147 600/114 |
| 2008/0287961 | A1* | 11/2008 | Miyamoto | A61B 1/018 606/127 |
| 2015/0057537 | A1* | 2/2015 | Dillon | A61B 1/0014 600/113 |
| 2016/0198936 | A1 | 7/2016 | Sueyasu et al. | |
| 2017/0319828 | A1 | 11/2017 | Doepker et al. | |
| 2019/0365203 | A1 | 12/2019 | Tyson et al. | |
| 2020/0108236 | A1 | 4/2020 | Salazar et al. | |
| 2022/0296078 | A1 | 9/2022 | Suzuki et al. | |

OTHER PUBLICATIONS

European Patent Office. Extended European Search Report for EP Application No. 23219537.0, mailed Aug. 26, 2024, pp. 1-11.

* cited by examiner 210
202
200
204
206
218

220
210

210
218
210
222

210
218
222

ENDOSCOPE HANDLE WITH CATHETER LOOP

RELATED APPLICATIONS

This application is a non-provisional application which claims priority under 35 USC § 119 to U.S. provisional application Ser. No. 63/476,747, filed Dec. 22, 2022, which is incorporated by reference herein in its entirety.

BACKGROUND

The statements in this section merely provide background information related to the present disclosure and may not constitute prior art.

Internal body cavities and body lumens may become blocked, or the walls surrounding them may develop growths. In some cases, removal of these blockages or growths, or other treatment thereof, may be necessary. Endoscope or other minimally invasive techniques may be used to treat these situations.

One type of treatment includes the use of catheters or other endoscopic devices that are inserted into the body lumen or cavity and toward the area where treatment is desired. Insertion of the endoscope to the target area can allow for visualization of the target area and a determination of the desired procedure and the specific location of the area to be treated.

In general, endoscopes have been designed to be operated with the same fundamental mechanisms, and have not had transformational improvements. Endoscopes generally include a camera and a set of wheels that an operator, such as a physician, operates with a first hand (in some cases, the left hand) to control scope deflection, while the second (generally, right) hand switches between the insertion tube of the endoscope and the accessory channel in order to control scope and device advancement, respectively, through the anatomy of a patient.

Available cholangioscopes are separate, disposable endoscopes that externally mount to a side of a duodenoscope and may pass through an accessory channel of a duodenoscope. Such a cholangioscope contains a loop of catheter between the duodenoscope accessory port and the cholangioscope handle that may allow a user to advance the cholangioscope further into the accessory channel by reducing the size of the loop. However, the presence of the loop in the catheter may be ergonomically unappealing, and further at risk of catching on corners of tables, nearby poles, and other objects. Commercially available devices that have a separate duodenoscope offer a user the option to choose if a cholangioscope is needed. The presence of a cholangioscope catheter loop near the handle may dissuade a user from using a cholangioscope, instead of a standard duodenoscope and cholangioscope system, unless the user definitively knows the user will be performing a cholangioscopy procedure. Even if a user is planning on performing a cholangioscopy procedure, the user may be frustrated with the presence of the loop before performing a cholangioscopy.

BRIEF SUMMARY

In an example, the present disclosure provides a scope system. The scope system includes a handle configured to move from a locked configuration to an unlocked configuration. The scope system further includes a stationary member including an elongate tube connected to the handle. The scope system further includes a movable elongate member including a tubular body with a proximal end and a distal end. When the handle is in the locked configuration, the movable elongate member is stored on a surface of the handle. When the handle is in the unlocked configuration, the proximal end of the movable elongate member is attached to the handle, and the movable elongate member is movably disposed within the elongate tube. The movable elongate member may further include an access channel extending at least partially longitudinally therethrough, the access channel configured to receive a wireguide or instrument. The movable elongate member may further include one or more channels extending at least partially longitudinally therethrough, the one or more channels configured to provide insufflation of gas, suction, and/or irrigation liquid to the distal end. The movable elongate member may further include a camera at the distal end. The movable elongate member may further include pull wires extending longitudinally therethrough. The movable elongate member may further include one or more light fibers or LEDs at the distal end. The handle may include one or more retaining tabs configured to secure the movable elongate member on the surface of the handle when the handle is in the locked configuration. The scope system may further include a removable handle lock configured to maintain the handle in the locked configuration until the removable handle lock is removed. The removable handle lock may be configured to prevent access to a working channel access port on the handle. The removable handle lock may be configured to prevent a rotating mode selection knob on the handle from being rotated. The removable handle lock may be configured to prevent the movable elongate member from being removed from the one or more retaining tabs on the surface of the handle. The removable handle lock may be connected to the handle when the handle is in the unlocked configuration.

In another example, the present disclosure provides a method of using a scope system. The method includes grasping a removable lock attached to a handle of the scope system, the handle in a locked configuration, the scope system including a stationary member including an elongate tube connected to the handle, and a movable elongate member including a tubular body with a proximal end and a distal end. The method further includes removing the removable handle lock from the handle. The method further includes attaching the proximal end of the movable elongate member to the handle. The method further includes advancing the distal end of the movable elongate member through the elongate tube toward a distal end of the scope system. The advancing may include manually moving a portion of the movable elongate member. The advancing may include moving an external mechanism. The external mechanism may include a wheel, lever, or sliding feature.

In yet another example, the present disclosure provides a scope system. The scope system includes a handle configured to move from a locked configuration to an unlocked configuration. The scope system further includes a stationary member including an elongate tube connected to the handle. The scope system further includes a movable elongate member including a tubular body with a proximal end and a distal end, the tubular body including a skive between the proximal end and the distal end. When the handle is in the locked configuration, the movable elongate member is stored on a surface of the handle. When the handle is in the unlocked configuration, the proximal end of the movable elongate member is attached to the handle, and the movable elongate member is movably disposed within the elongate tube. The movable elongate member may further include an access channel extending at least partially longitudinally therethrough, the access channel configured to receive a wireguide or instrument entering through the skive. The movable elongate member may further include a camera at the distal end, a cable for the camera entering the movable elongate member through the skive. The movable elongate member may further include one or more light fibers or LEDs at the distal end, a cable for the one or more light fibers or LEDs entering the movable elongate member through the skive.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

In order that the present disclosure may be well understood, there will now be described various forms thereof, given by way of example, reference being made to the accompanying drawings. The components in the figures are not necessarily to scale. Moreover, in the figures, like-referenced numerals designate corresponding parts through the different views.

Figure 1A:
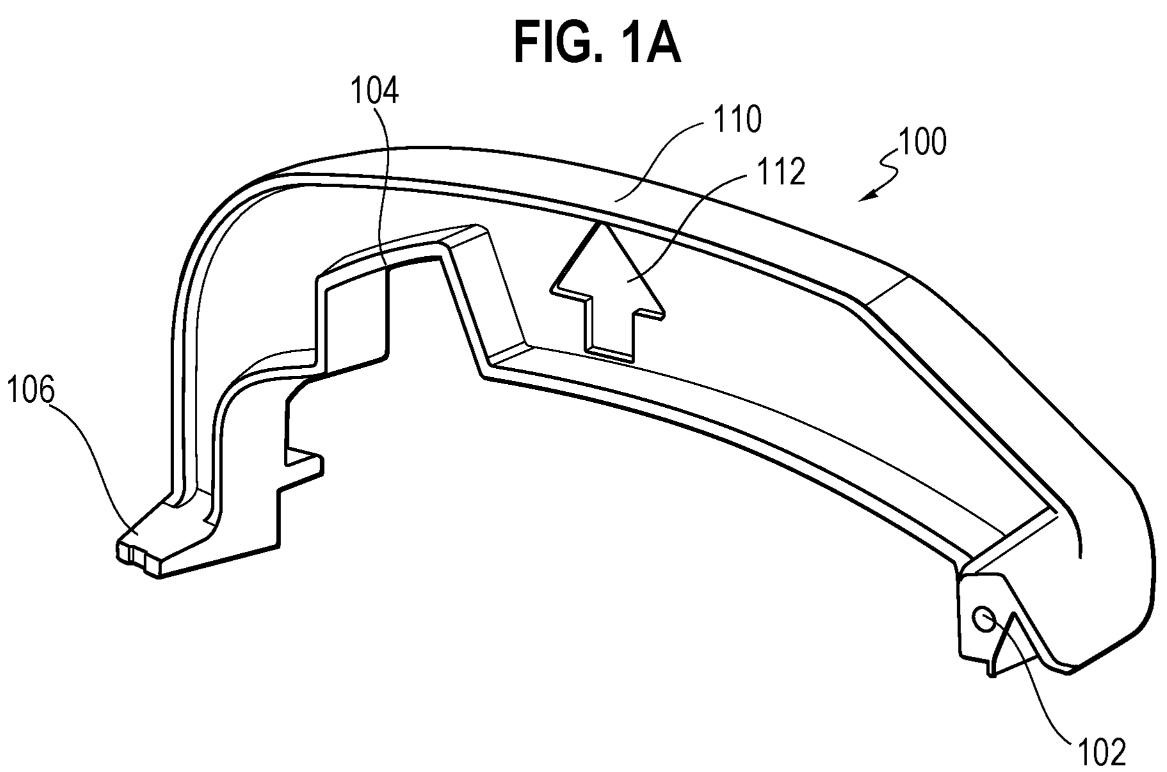
FIG. 1A illustrates a partial perspective view of an example of a removable handle lock according to the principles of the present disclosure.

The drawings described herein are for illustration purposes only and are not intended to limit the scope of the present disclosure in any way.

DETAILED DESCRIPTION OF THE DRAWINGS

The following description presents examples and is not intended to limit the present disclosure, application, or uses. It should be understood that throughout the drawings, corresponding reference numerals indicate like or corresponding parts and features.

In adding reference denotations to elements of each drawing, although the same elements are displayed on a different drawing, it should be noted that the same elements have the same denotations. In addition, in describing one aspect of the present disclosure, if it is determined that a detailed description of related well-known configurations or functions blurs the gist of one aspect of the present disclosure, it will be omitted.

In the following discussion, the terms “proximal” and “distal” will be used to describe the opposing axial ends of the device, as well as the axial ends of various component features. The term “proximal” is used in its conventional sense to refer to the end of the device (or component) that is closest to the medical professional during use of the assembly. The term “distal” is used in its conventional sense to refer to the end of the device (or component) that is initially inserted into the patient, or that is closest to the patient during use. The term “longitudinal” will be used to refer to an axis that aligns with the proximal-distal axis of the device (or component). The terms “radially” and “radial” will be used to refer to elements, surfaces, or assemblies relative to one another that may extend perpendicularly from a longitudinal axis. The terms “circumference,” “circumferentially,” and “circumferential” will be used to refer to elements, surfaces, or assemblies relative to one another encircling a longitudinal axis at a radius.

The uses of the terms “a” and “an” and “the” and similar referents in the context of describing the present disclosure (especially in the context of the following claims) are to be construed to cover both the singular and the plural, unless otherwise indicated herein or clearly contradicted by context. The use of the term “plurality of” is defined by the Applicant in the broadest sense, superseding any other implied definitions or limitations hereinbefore or hereinafter unless expressly asserted by the Applicant to the contrary, to mean a quantity of more than one. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As used herein, the terms “comprise(s),” “include(s),” “having,” “has,” “can,” “contain(s),” and variants thereof, are intended to be open-ended transitional phrases, terms, or words that do not preclude the possibility of additional acts or structures. The present description also contemplates other examples “comprising,” “consisting of,” and “consisting essentially of,” the examples or elements presented herein, whether explicitly set forth or not.

In describing elements of the present disclosure, the terms 1st, 2nd, first, second, A, B, (a), (b), and the like may be used herein. These terms are only used to distinguish one element from another element, but do not limit the corresponding elements irrespective of the nature or order of the corresponding elements.

Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art.

As used herein, the term "about," when used in the context of a numerical value or range set forth means a variation of ±15%, or less, of the numerical value. For example, a value differing by ±15%, ±14%, ±10%, or ±5%, among others, would satisfy the definition of "about," unless more narrowly defined in particular instances.

Referring to FIG. 1A, a perspective view of an example of a removable handle lock 100 is illustrated. Removable handle lock 100 may simultaneously lock a cholangioscope loop (not shown) in position on a side of an endoscope handle, prevents inadvertent access of the cholangioscope working channel access port, and prevents the mode selector from being inadvertently rotated to cholangioscope mode. Removable handle lock 100 includes cholangioscope bore 102 configured to be reversibly occupied by a cholangioscope loop when the cholangioscope loop is stored on the side of the endoscope handle. Removable handle lock 100 includes access port cover portion 104 shaped to at least approximate, or confront, the cholangioscope working channel access port in the endoscope handle and thereby cover the access port, providing a safety feature by preventing unintentional access to the wire guide channel when the endoscope is in duodenoscope mode. Removable handle lock 100 further includes rotational stop 106 which prevents the rotating mode selector feature (not shown) on the endoscope handle from inadvertently switching between duodenoscope mode and cholangioscope mode.

Figure 1B:
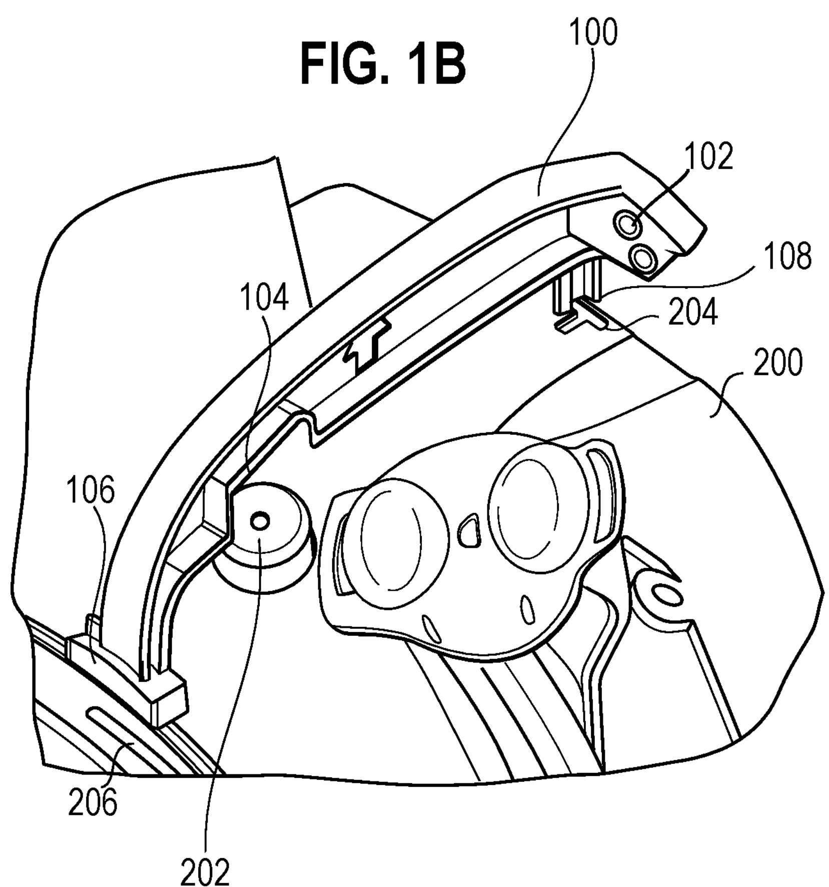
FIG. 1B illustrates another perspective view of the example of a removable handle lock illustrated in FIG. 1A and a partial view of a handle of a scope system, with tabs of the lock in alignment above corresponding slots in the handle, according to the principles of the present disclosure.

Referring to FIG. 1B, another perspective view of the example of removable handle lock 100 and a partial perspective view of an example of an endoscope handle 200 of a scope system is illustrated. The removable handle lock 100 is positioned in alignment with complementary engaging slots on handle 200. Access port cover portion 104 is illustrated above access port 202 such that when removable handle lock 100 is reversibly engaged with handle 200, access port 202 will be blocked from inadvertent access to the wire guide channel. Removable handle lock 100 includes tab 108 configured to reversibly engage with slot 204 of handle 200 such that removable handle lock 100 securely locks endoscope handle when removable handle lock 100 is applied. Rotational stop 106 is configured to reversibly engage with rotational slot 206 of handle 200 such that removable handle lock 100 securely locks endoscope handle when removable handle lock 100 is applied.

Figure 1C:
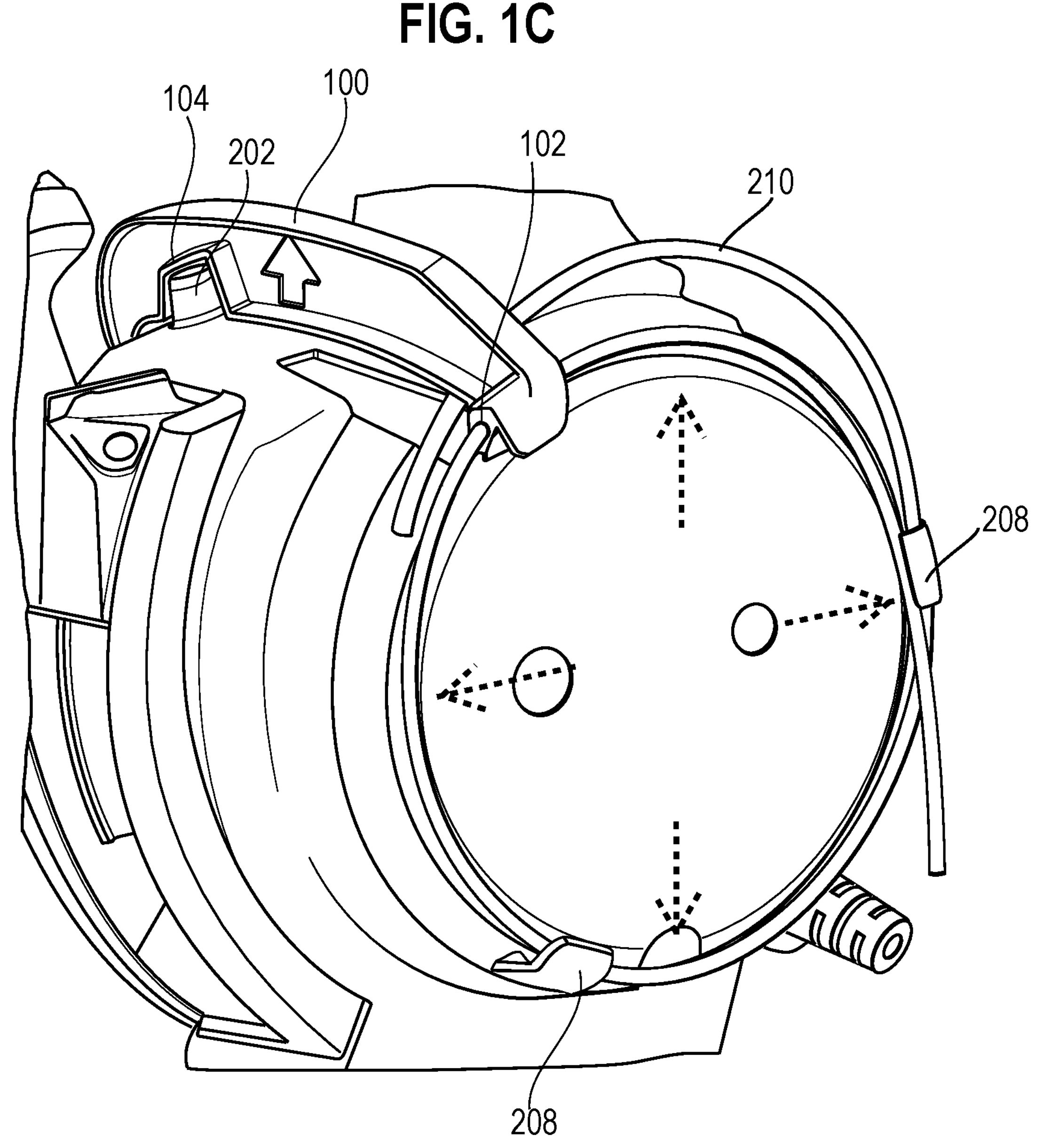
FIG. 1C illustrates a partial perspective view of the example of the removable handle lock illustrated FIG. 1A engaged with the example of the handle illustrated in FIG. 1B, according to the principles of the present disclosure.

Referring to FIG. 1C, another perspective view of the example of removable handle lock 100 and a partial perspective view of the example of endoscope handle 200 of a scope system is illustrated, in which removable handle lock 100 is engaged with handle 200 to prevent switching from duodenoscope mode to cholangioscope mode.

FIG. 1C corresponds to an example of a first configuration for handle 200. Handle 200 includes cholangioscope loop 210 wound up and stored, cholangioscope loop 210 reversibly inserted through cholangioscope bore 102 of removable handle lock 100 and retaining tab(s) 208 configured to hold wound cholangioscope loop 210. Cholangioscope loop 210 as wound and stored may naturally exert an outward radial force against retaining tab(s) 208 and thereby remain in place within retaining tab(s) 208 as illustrated by arrows in FIG. 1C. By winding up and storing cholangioscope loop 210 on the side of handle 200, cholangioscope loop 210 may be substantially smaller and may face away to the side of a user of handle 200, and may thereby be less likely to catch on or interact with unintended surfaces in front of a user as maneuvers are performed. FIG. 1C further illustrates access port cover portion 104 locked in place around access port 202 such that access port 202 is blocked from inadvertent access to the wire guide channel.

Figure 1D:
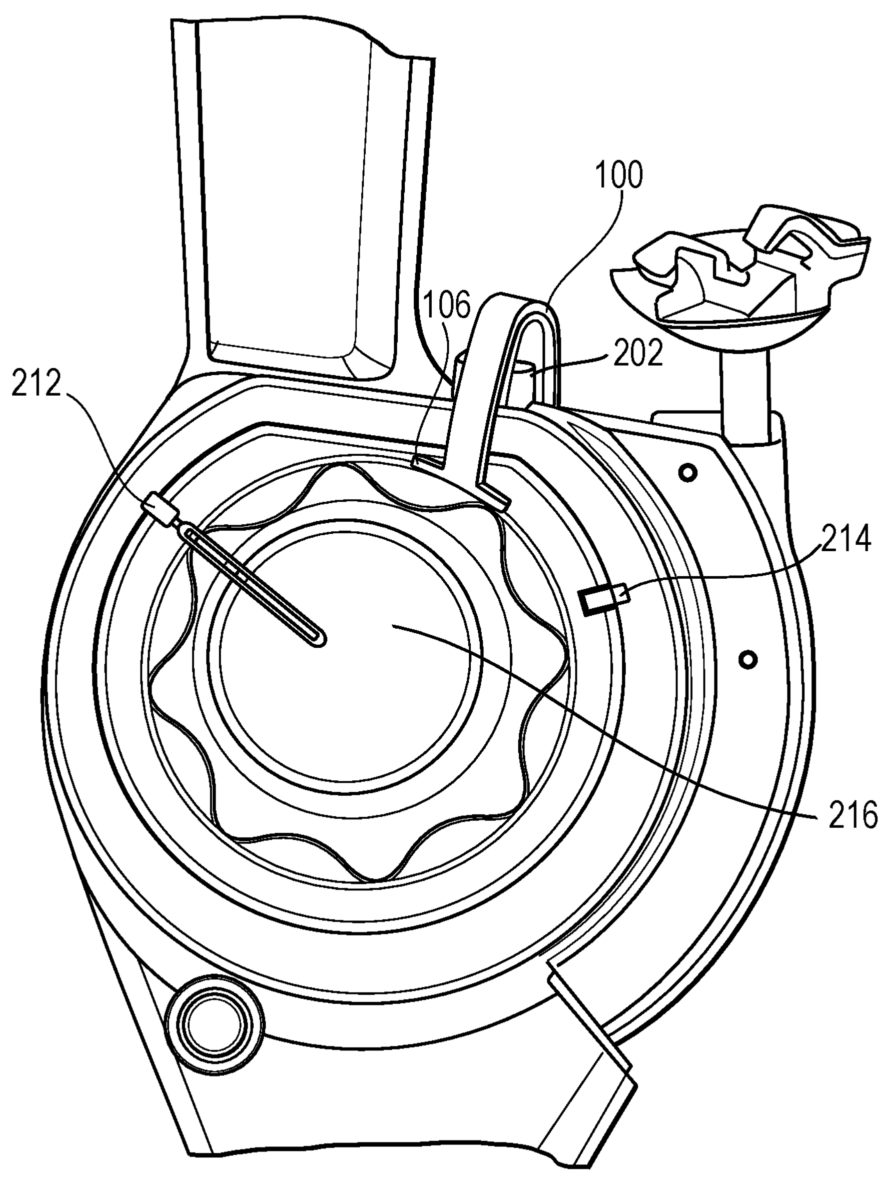
FIG. 1D illustrates a side view of the example of the removable handle lock engaged with the example of the handle as illustrated in FIG. 1C, according to the principles of the present disclosure.

Referring to FIG. 1D, a side view of the example of removable handle lock 100 reversibly engaged with the example of endoscope handle 200 of a scope system is illustrated. FIG. 1D illustrates removable handle lock 100 and endoscope handle 200 from a direction almost opposite the view illustrated in FIG. 1C. In FIG. 1D, the side of handle 200 opposite the side including the cholangioscope loop 210 wound and stored within retaining tab(s) 208 is illustrated. FIG. 1D illustrates a rotating mode selection knob 216, which a user may rotate between duodenoscope mode rotational setting 212 and cholangioscope mode rotational setting 214. Rotational stop 106 of removable handle lock 100 may prevent a user from moving rotating mode selection knob 216 from the duodenoscope mode rotational setting 212 to cholangioscope mode rotational setting 214. Rotational stop 106 may prevent rotating mode selection knob 216 from being rotated inadvertently, thereby avoiding changing modes of operation unexpectedly.

The attachment force of removable handle lock 100 may be such that removable handle lock 100 may be easily manually removed when a user wishes to transition from a first configuration to a second configuration. Removable handle lock 100 may have a suitable grasping feature 110 such that removable handle lock 100 may be manually grasped and removed when a user wishes to transition from a first configuration to a second configuration. Removable handle lock 100 may include a removal direction indication feature 112 that may indicate a direction by which the removable handle lock 100 should be removed when a user wishes to transition from a first configuration to a second configuration. Removable handle lock 100 may have a color visually distinct from handle 200 so as to differentiate removable handle lock 100 to a user and make removable handle lock 100 more visible when a user wishes to transition from a first configuration to a second configuration. Removable handle lock 100 may include a secondary connection between removable handle lock 100 and handle 200 such that when removable handle lock 100 is removed, removable handle lock 100 may be easily located for subsequent reattachment. Examples of such a secondary connection may include a flexible cord-based tether and a hinge.

By having two configurations, including the first configuration illustrated in FIGS. 1C and 1D, an endoscope system may be more intuitive for a user, who may be used to currently commercially available endoscope systems, in which a procedure may be started with a duodenoscope like in the first configuration, before the endoscope system is transitioned to a duodenoscope with an attached cholangioscope. The two different configurations may reduce the training requirement for users who are trained on the commercially available first configuration.

Figures 2A, 2B:
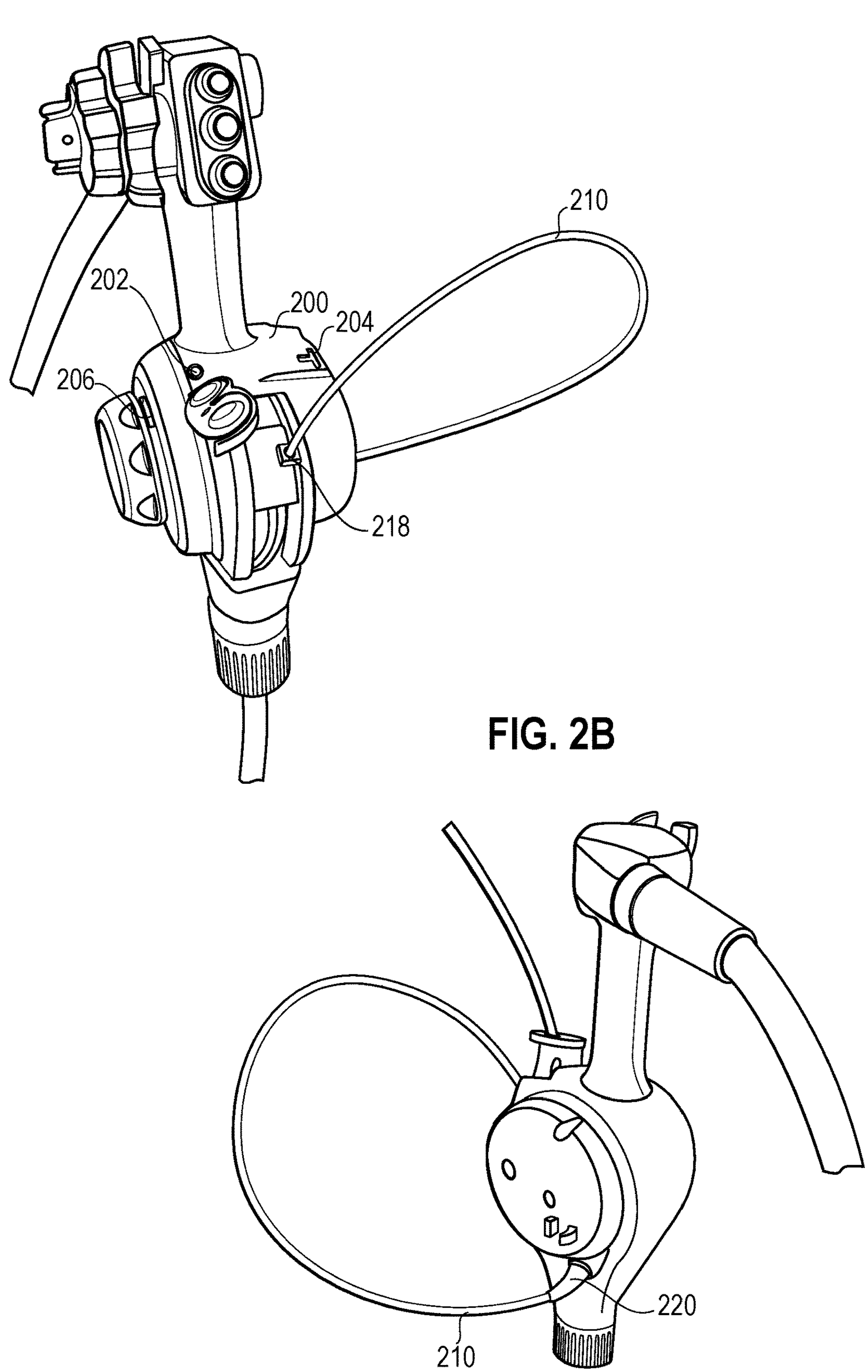
FIG. 2A illustrates a perspective view of an example of a handle of a scope system with the removable handle lock removed, and an example of a cholangioscope loop unwound and ready for use, according to the principles of the present disclosure.
FIG. 2B illustrates another perspective view of the example of the handle illustrated in FIG. 2A, according to the principles of the present disclosure.

Referring to FIG. 2A, a perspective view of an example of a handle of a scope system, in which the removable handle lock has been removed, and including an example of a cholangioscope loop 210 unwound and ready for use, is illustrated. FIG. 2A corresponds to an example of a second configuration for handle 200. Cholangioscope loop 210 is attached to handle 200 at entry port 218 so as to provide cholangioscope loop 210 with an ergonomic shape and position. Cholangioscope working channel access port 202 may be located in an ergonomically advantageous shape and position in the mid-section of handle 200, such that a trajectory of an accessory in access port 202 may advantageously point away from a user, and such that a wireguide may travel a shorter distance through cholangioscope loop 210. Together, the design aspects illustrated in FIG. 2A may provide superior performance compared to currently available combined duodenoscope/cholangioscope configurations.

Referring to FIG. 2B, a perspective view of the example of a handle of a scope system illustrated in FIG. 2A is illustrated. Cholangioscope loop 210 exits handle 200 at exit point 220, which is located to further provide cholangioscope loop 210 with an ergonomic shape and position.

Figures 2C, 2D:
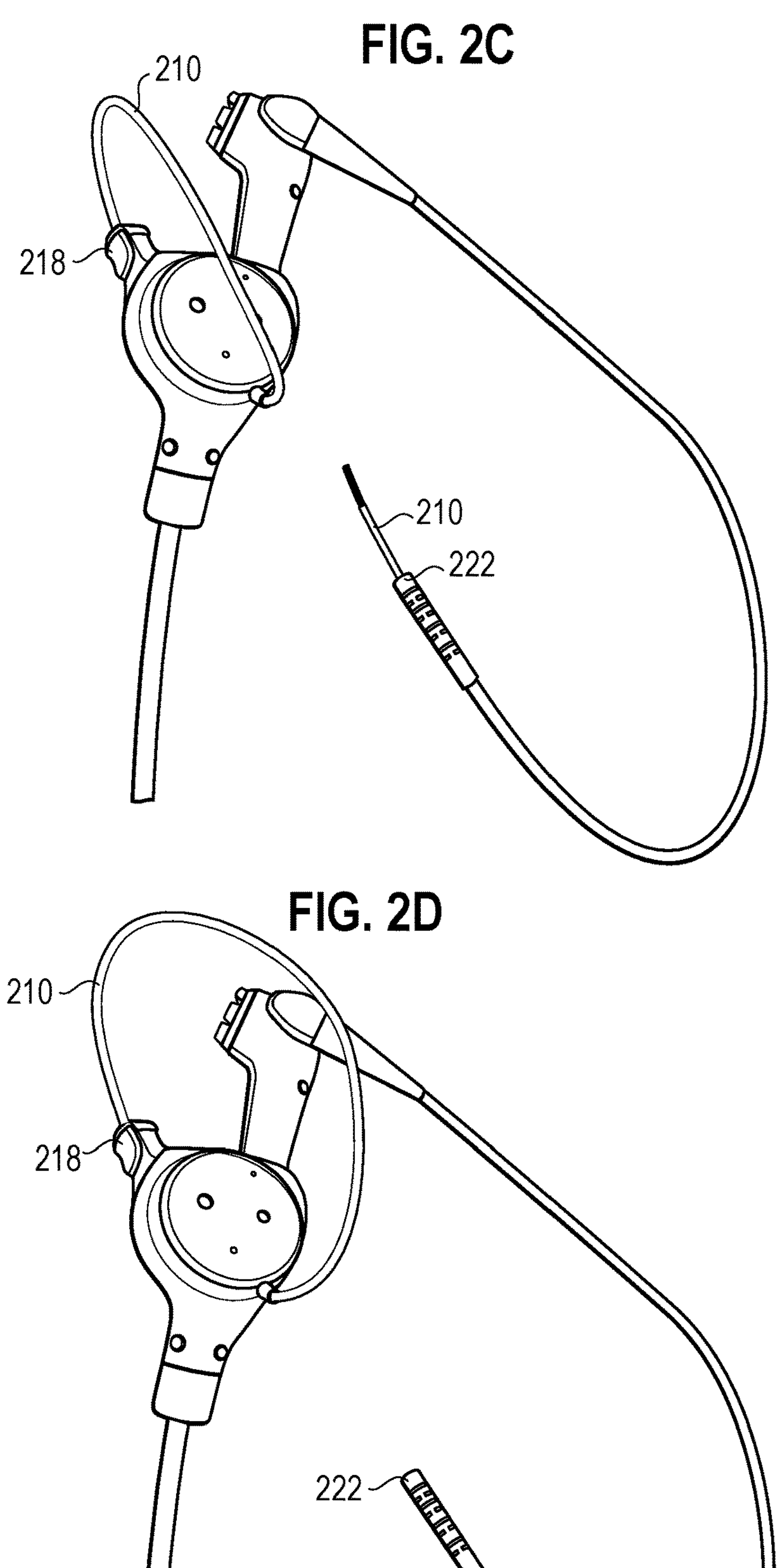
FIG. 2C illustrates a side view of the example of the handle illustrated in FIGS. 2A and 2B, with an example of a cholangioscope catheter loop pushed into an entry port of the handle and exiting from a distal end of the scope system, according to the principles of the present disclosure.
FIG. 2D illustrates a side view of the example of the handle and distal end of the scope system illustrated in FIG. 2C, with the cholangioscope catheter loop not pushed into the handle and consequently not exiting from the distal end, according to the principles of the present disclosure.

Referring to FIG. 2C, a side view of the example of a handle of a scope system illustrated in FIGS. 2A and 2B, is illustrated. In FIG. 2C, cholangioscope loop 210 is illustrated pushed into an entry port 218 in handle 200 and shown exiting from a distal end 222 of the endoscope system. By contrast, in FIG. 2D, cholangioscope loop 210 is illustrated as not having been pushed into entry port 218 in handle 200 as far as is illustrated in FIG. 2C. Consequently, by not being pushed into entry port 218 in handle 200 as far in FIG. 2D, cholangioscope loop 210 does not exit from distal end 222.

Cholangioscope loop 210 may include a working or access channel that may be configured to allow a wire guide or instrument to be passed through the cholangioscope loop 210, such that the wire guide or instrument may exit at the distal end of the cholangioscope loop 210. The wire guide or instrument may enter the working or access channel at the proximal end of the cholangioscope loop 210 or through a skive, distal to the proximal end. Examples of an instrument may include an electrohydraulic lithotripsy ("EHL") probe, biopsy forceps, a basket, and snares.

Cholangioscope loop 210 may include one or more channels providing for insufflation of gas, suction, and irrigation of liquid through cholangioscope loop 210 at the proximal end of the cholangioscope loop 210 or distal to the proximal end, through a skive.

Cholangioscope loop 210 may include a camera at a distal end, the cable for which either enters into cholangioscope loop 210 through the proximal end of the cholangioscope loop 210, or distal to the proximal end, through a skive.

Cholangioscope loop 210 may include one or more pull wires that may enter cholangioscope loop 210 through the proximal end of the cholangioscope loop 210.

Cholangioscope loop 210 may include a light fiber at the distal end, or electrical wires to power a light-emitting diode ("LED") at the distal end, the wires for the LED entering cholangioscope loop 210 at the proximal end, or distal to the proximal end through a skive.

An operator may advance cholangioscope loop 210 relative to the handle by manipulation of the cholangioscope loop 210 or by an external mechanism that is connected to a mechanism inside of the handle that advances the cholangioscope loop 210 in response to manipulation of the external mechanism.

Figure 3A:
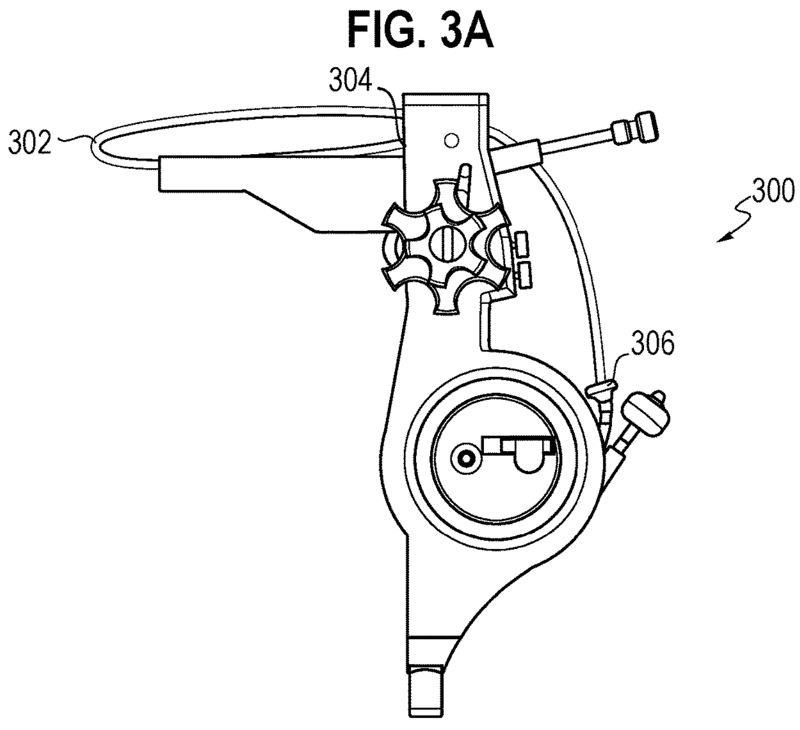
FIG. 3A illustrates a side view of another example of a handle in forward-viewing mode, with a cholangioscope catheter loop exiting the handle behind a user, according to the principles of the present disclosure.
Figure 3B:
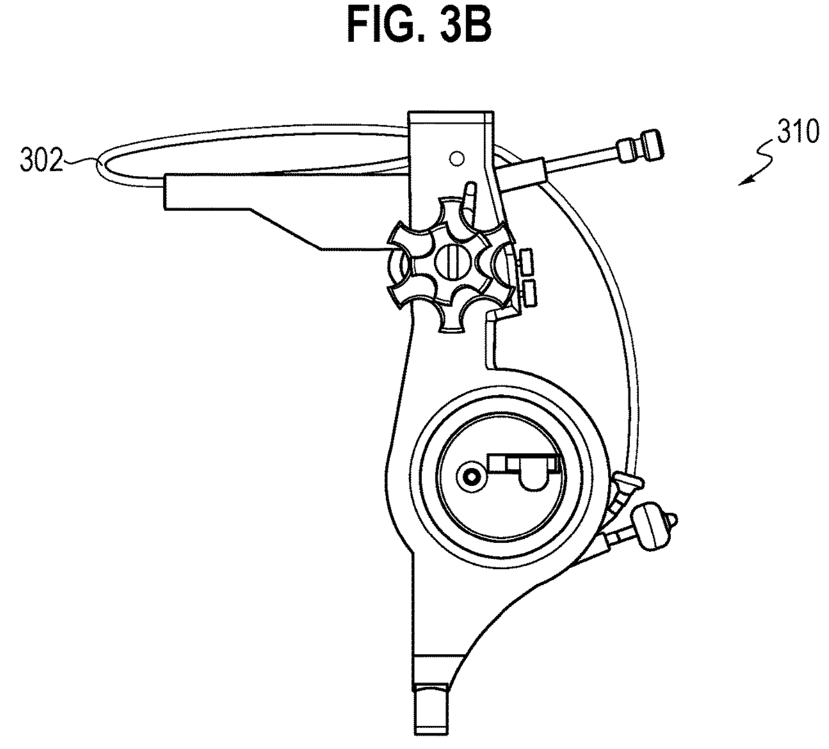
FIG. 3B illustrates a side view of the example of the handle illustrated in FIG. 3A in side-viewing mode, according to the principles of the present disclosure.

Referring to FIG. 3A, a side view of another example of a handle 300 in forward-viewing mode, with cholangioscope loop 302 exiting the handle 300 behind a user, is illustrated. Cholangioscope loop 302 may loop out from the proximal end 304 of the handle 300 and return into the handle at entry port 306, and from the handle 300 travel to the distal end of the scope system. FIG. 3B illustrates a side view of an example of a handle 310 in side-viewing mode.

The terms "forward-viewing mode" and "side-viewing mode" refer to the fact that a distal end of accessory channels within endoscope system may be secured to a pivot arm at the distal end of the endoscope system (not shown here, but readily understandable to those of skill in the art, including by way of non-limiting example to embodiments shown in FIGS. 13-16 of U.S. Pat. App. Publ. 2021/0401270, which is incorporated herein by reference in its entirety). Therefore, the accessory channels, and the view through a scope, may rotate with the pivot arm when moving the pivot arm between the side-viewing and forward-viewing modes. A forward-viewing mode refers to a mode in which a scope has a view coaxial with the longitudinal axis of the distal end of the endoscope system. A side-viewing mode refers to a mode in which the scope has a view that is not a forward-viewing mode by virtue of the scope rotating with the pivot arm.

In handle 300, instead of cholangioscope loop 302 being positioned in front of handle 300, cholangioscope loop 302 is located behind the handle, facing away from a user and less likely to catch on items in front of the user as maneuvers are performed. Cholangioscope loop 302 may sit above the umbilical cord so that cholangioscope loop 302 follows the initial proximal trajectory of the umbilical cord away from handle 300. An additional member may be clamped onto the umbilical cord to protect cholangioscope 302. The additional member may be flexible, such as an overtube, or a flexible molded plastic snap-on piece. Cholangioscope loop 302 may subsequently exit the front of handle 300 and then re-enter handle 300 to terminate at the distal end of the device such that a user may grasp the cholangioscope loop 302 to advance or retract the cholangioscope loop 302 similarly to other cholangioscope systems. When the cholangioscope is not in use, the user may clamp the graspable aspect of cholangioscope loop 302 to handle 300 so cholangioscope loop 302 is out of the way completely when cholangioscope is not in use. The graspable aspect is clamped by such mechanism as a mating snap-on feature on handle 300. Although in FIGS. 3A and 3B, the cholangioscope loop 302 is illustrated in a certain plane relative to handle 300, other planes may be used for optimal ergonomic interaction, or cholangioscope 302 may more closely hug the body of handle 300 prior to being grasped by a user to advance.

In another configuration, an external feature may be added to protect cholangioscope loop 302 from handle 300 except for the section the user will grasp to advance cholangioscope loop 302. Such an external feature may be a circular protective extrusion from handle 300, or a flexible loose reinforcement material placed over cholangioscope loop 302 that snaps onto handle 300.

To achieve cholangioscope loop 302 exiting behind the scope, some adjustments may be necessary internally. Specifically, instead of pullwires facing downwards toward the distal end of the scope system, pullwires may be directed upwards toward the umbilical cord. An internal feature may support the pullwires before porting into cholangioscope loop 302 so they do not interfere with other features within handle 300 such as the internal wheel mechanisms and fluid lines. Further, due to limitations in the functional distance that can be achieved with light fiber optics and camera chip data streams, it is preferably to minimize the distance of the specific members from the camera board to the distal end of the device. To minimize the distance, a skive may run along a length of cholangioscope loop 302 whereby the camera chip cable and light fiber cable enter into the cholangioscope. The length of the skive may depend on the necessary length required for the cholangioscope to exit at the distal end of the device for cholangioscopy procedures. The porting of pull wires and fluid lines may occur at the proximal end of cholangioscope loop 302, but the fiber optic and camera chip cable may enter cholangioscope loop 302 distal to the proximal end via a skive of a certain length.

In an example, the present disclosure provides an endoscope including a stationary first member running from the distal end of the handle to the distal end of the endoscope and a movable elongate member that starts at the proximal end of the handle, loops out, returns into the handle, and travels to the distal end of the endoscope. The movable member is within the first member.

In another example, the movable elongate member may include a camera at the distal end, the camera cable of which either enters into the movable member at the proximal end or distal to the proximal end through a skive.

In yet another example, the movable elongate member may include pull wires that enter into the movable member at the proximal end.

In yet another example, the movable elongate member may include a light fiber at the distal end of the movable member, the light fiber cable entering into the movable member at the proximal end of the movable member or distal to the proximal end through a skive.

In yet another example, a user may engage with the movable elongate member to advance the movable member either at the portion of the loop, or once the movable member returns into the first member through an external mechanism.

In yet another example, the endoscope may include a feature to clip the movable member to the umbilical cord. The feature may be stationary or movable, such as a slide.

In yet another example, the endoscope may include a feature to clip the movable member to the first member when the movable member is not in use.

In an example, the present disclosure provides an endoscope including a stationary first member running from the distal end of the handle to the distal end of the endoscope and a movable elongate member that starts at the proximal end of the handle, loops out, returns into the handle, exits the handle again, returns into the handle, and travels to the distal end of the endoscope. The movable member is within the first member.

Figure 4:
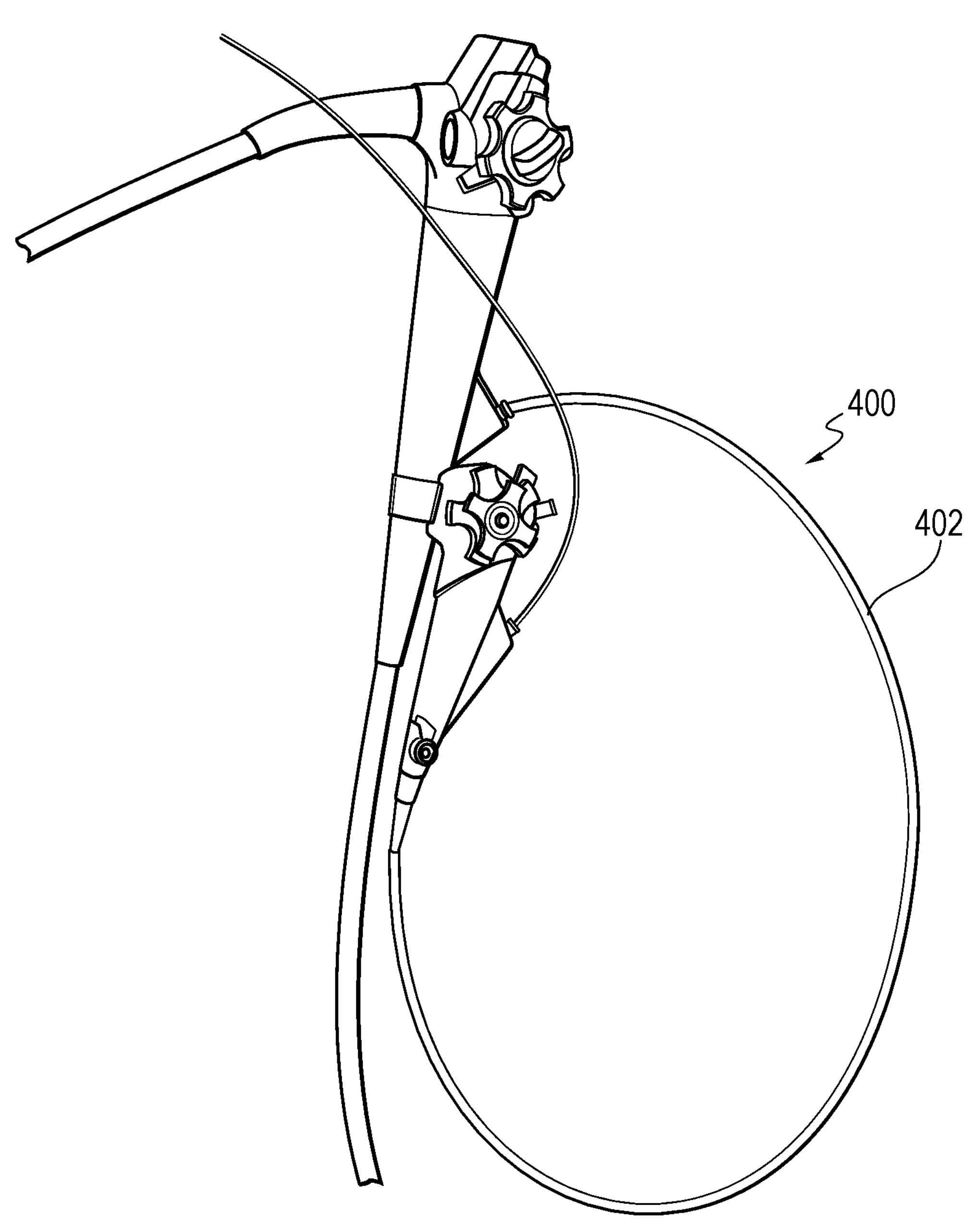
FIG. 4 illustrates a perspective view of an example of an endoscope system including an example of a large and undesirable cholangioscope catheter loop.

Referring to FIG. 4, a perspective view of an example of an endoscope system 400 including an example of a large and undesirable cholangioscope loop 402 is illustrated. Cholangioscope loop 402 is large and awkward, and may dissuade users from using endoscope system 400 unless a user knew that cholangioscopy would be performed compared to standard duodenoscopy. Cholangioscope loop 402 may not be ergonomically appealing and may be at risk of catching on a table or nearby pole.

In an example, the present disclosure provides an endoscope in which the cholangioscope enters into the umbilical cord, forms a loop within the umbilical cord, then re-enters the handle and terminates at the distal end of the device. So as to minimize friction and magnify the force on the catheter in the umbilical cord, a pulley system or slider may be used to directly move the catheter instead of pulling the catheter from a distal point, which may potentially result in a reduction in force or formation of a kink in the camera catheter.

In another example, the user interface may actuate advancement and/or retraction of the catheter. Instead of the catheter exiting the handle for the user to grip and advance, an ergonomically advantageous opening for the user to grip the cholangioscope may be added within the handle, such as a window within the handle near the wheels through which to grip the catheter.

In yet another example, the catheter may be completely hidden within the handle and an external mechanism such as a wheel, lever, or sliding feature may be used to advance the catheter. If a wheel is used, an internal feature may grip the catheter to advance the catheter, whereby different materials or shapes may be used to grip the catheter without damaging the catheter and to advance the catheter. If a slider is used, the slider may be directly coupled to the catheter, or a rack and pinion may be used to change the ratio of travel of the slider versus displacement of the catheter. In any of these concepts, gears may be used to create a ratio to optimize the motion of the external interface to the actual displacement of the catheter. An external switch may be added to switch between gear ratios for fine control of displacement to coarse control of catheter displacement with the same external interface.

In yet another example, an endoscope includes a stationary first member running from the distal end of the handle to the distal end of the device. The endoscope includes a movable elongate member that starts at the proximal end of the handle, forms a loop proximal to the handle or within the handle, and travels to the distal end of the device. The movable member is within the first member. A user may move the movable member through an external interface on the handle. The external interface may be a wheel. The internal interface to the movable member may be a member that grips the movable member with a frictional material or with a shape and through rotation advances the movable member in a linear fashion. The internal interface to the movable member may be a sliding member engaging the external interface through an external slider, or a rotational wheel through a rack/pinion design. The internal interface may include gear(s) to create an optimal ratio for external movement to internal displacement. A switch may interface with multiple gears to create multiple gear ratios for both fine motion control and coarse motion control of the camera catheter.

Although the present disclosure has been described with reference to examples and the accompanying drawings, the present disclosure is not limited thereto, but may be variously modified and altered by those skilled in the art to which the present disclosure pertains without departing from the spirit and scope of the present disclosure.

The subject-matter of the present disclosure may also relate, among others, to the following aspects:

A first aspect relates to a scope system, comprising: a handle configured to move from a locked configuration to an unlocked configuration; a stationary member comprising an elongate tube connected to the handle; a movable elongate member comprising a tubular body with a proximal end and a distal end; wherein, when the handle is in the locked configuration, the movable elongate member is stored on a surface of the handle; and wherein, when the handle is in the unlocked configuration, the proximal end of the movable elongate member is attached to the handle, and the movable elongate member is movably disposed within the elongate tube.

A second aspect relates to the scope system of aspect 1, wherein the movable elongate member further comprises an access channel extending at least partially longitudinally therethrough, the access channel configured to receive a wireguide or instrument.

A third aspect relates to the scope system of any preceding aspect, wherein the movable elongate member further comprises one or more channels extending at least partially longitudinally therethrough, the one or more channels configured to provide insufflation of gas, suction, and/or irrigation liquid to the distal end.

A fourth aspect relates to the scope system of any preceding aspect, wherein the movable elongate member further comprises a camera at the distal end.

A fifth aspect relates to the scope system of any preceding aspect, wherein the movable elongate member further comprises pull wires extending longitudinally therethrough.

A sixth aspect relates to the scope system of any preceding aspect, wherein the movable elongate member further comprises one or more light fibers or LEDs at the distal end.

A seventh aspect relates to the scope system of any preceding aspect, wherein the handle comprises one or more retaining tabs configured to secure the movable elongate member on the surface of the handle when the handle is in the locked configuration.

An eighth aspect relates to the scope system of any preceding aspect, further comprising a removable handle lock configured to maintain the handle in the locked configuration until the removable handle lock is removed.

A ninth aspect relates to the scope system of aspect 8, wherein the removable handle lock is configured to prevent access to a working channel access port on the handle.

A tenth aspect relates to the scope system of aspects 8 or 9, wherein the removable handle lock is configured to prevent a rotating mode selection knob on the handle from being rotated.

An eleventh aspect relates to the scope system of aspects 8 to 10, wherein the removable handle lock is configured to prevent the movable elongate member from being removed from the one or more retaining tabs on the surface of the handle.

A twelfth aspect relates to the scope system of aspects 8 to 11, wherein the removable handle lock is connected to the handle when the handle is in the unlocked configuration.

A thirteenth aspect relates to the scope system of any preceding aspect, wherein the tubular body comprises a skive between the proximal end and the distal end.

A fourteenth aspect relates to the scope system of aspect 13, wherein the access channel is configured to receive a wireguide or instrument entering through the skive.

A fifteenth aspect relates to the scope system of aspects 13 or 14, wherein the movable elongate member further comprises a camera at the distal end, a cable for the camera entering the movable elongate member through the skive.

A sixteenth aspect relates to the scope system of aspects 13 to 15, wherein the movable elongate member further comprises one or more light fibers or LEDs at the distal end, a cable for the one or more light fibers or LEDs entering the movable elongate member through the skive.

A seventeenth aspect relates to a method of using a scope system, comprising: grasping a removable handle lock attached to a handle of the scope system, the handle in a locked configuration, the scope system further comprising a stationary member comprising an elongate tube connected to the handle, and a movable elongate member comprising a tubular body with a proximal end and a distal end; removing the removable handle lock from the handle; attaching the proximal end of the movable elongate member to the handle; and advancing the distal end of the movable elongate member through the elongate tube toward a distal end of the scope system.

An eighteenth aspect relates to the method of aspect 17, wherein the advancing comprises manually moving a portion of the movable elongate member.

A nineteenth aspect relates to the method of aspects 17 or 18, wherein the advancing comprises moving an external mechanism.

A twentieth aspect relates to the method of aspect 19, wherein the external mechanism comprises a wheel, lever, or sliding feature.

In addition to the features mentioned in each of the independent aspects enumerated above, some examples may show, alone or in combination, the optional features mentioned in the dependent aspects and/or as disclosed in the description above and shown in the figures.

The invention claimed is:

1. A scope system, comprising:

a handle configured to move from a locked configuration to an unlocked configuration;

a stationary member comprising an elongate tube connected to the handle; and a movable elongate member comprising a tubular body with a proximal end and a distal end;

wherein, when the handle is in the locked configuration, the movable elongate member is stored on a surface of the handle; and wherein, when the handle is in the unlocked configuration, the proximal end of the movable elongate member is attached to the handle, and the movable elongate member is movably disposed within the elongate tube.

2. The scope system of claim 1, wherein the movable elongate member further comprises an access channel extending at least partially longitudinally therethrough, the access channel configured to receive a wireguide or instrument.

3. The scope system of claim 1, wherein the movable elongate member further comprises one or more channels extending at least partially longitudinally therethrough, the one or more channels configured to provide insufflation of gas, suction, and/or irrigation liquid to the distal end.

4. The scope system of claim 1, wherein the movable elongate member further comprises a camera at the distal end.

5. The scope system of claim 1, wherein the movable elongate member further comprises pull wires extending longitudinally therethrough.

6. The scope system of claim 1, wherein the movable elongate member further comprises one or more light fibers or LEDs at the distal end.

7. The scope system of claim 1, wherein the handle comprises one or more retaining tabs configured to secure the movable elongate member on the surface of the handle when the handle is in the locked configuration.

8. The scope system of claim 1, further comprising a removable handle lock configured to maintain the handle in the locked configuration until the removable handle lock is removed.

9. The scope system of claim 8, wherein the removable handle lock is configured to prevent access to a working channel access port on the handle.

10. The scope system of claim 8, wherein the removable handle lock is configured to prevent a rotating mode selection knob on the handle from being rotated.

11. The scope system of claim 8, wherein the removable handle lock is configured to prevent the movable elongate member from being removed from one or more retaining tabs disposed on the surface of the handle.

12. The scope system of claim 8, wherein the removable handle lock is connected to the handle when the handle is in the unlocked configuration.

13. A method of using a scope system according to claim 1, the method comprising:

grasping a removable handle lock attached to the handle of the scope system, with the handle in a locked configuration;

removing the removable handle lock from the handle;

attaching the proximal end of the movable elongate member to the handle; and advancing the distal end of the movable elongate member through the elongate tube toward a distal end of the scope system.

14. A scope system, comprising:

a handle configured to move from a locked configuration to an unlocked configuration;

a stationary member comprising an elongate tube connected to the handle; and a movable elongate member comprising a tubular body with a proximal end and a distal end, the tubular body comprising a skive between the proximal end and the distal end;

wherein, when the handle is in the locked configuration, the movable elongate member is stored on a surface of the handle; and wherein, when the handle is in the unlocked configuration, the proximal end of the movable elongate member is attached to the handle, and the movable elongate member is movably disposed within the elongate tube.

15. The scope system of claim 14, wherein the movable elongate member further comprises one or more channels extending at least partially longitudinally therethrough, the one or more channels configured to provide insufflation of gas, suction, and/or irrigation liquid to the distal end.

16. The scope system of claim 14, wherein the movable elongate member further comprises a camera at the distal end.

17. The scope system of claim 14, further comprising a removable handle lock configured to maintain the handle in the locked configuration until the removable handle lock is removed.

18. The scope system of claim 17, wherein the removable handle lock is configured to prevent access to a working channel access port on the handle.

19. The scope system of claim 17, wherein the removable handle lock is configured to prevent the movable elongate member from being removed from one or more retaining tabs disposed on the surface of the handle.

20. The scope system of claim 17, wherein the removable handle lock is connected to the handle when the handle is in the unlocked configuration.

* * * * *